US008463389B1

(12) United States Patent
Oths (10) Patent No.: US 8,463,389 B1
(45) Date of Patent: Jun. 11, 2013

(54) MULTI-SENSORY SYSTEM AND METHOD FOR PROVIDING NEUROMUSCULAR STIMULATION

(76) Inventor: Richard Oths, Nashville, TN (US)

(*) Notice: Subject to any disclaimer, the term of this patent is extended or adjusted under 35 U.S.C. 154(b) by 82 days.

(21) Appl. No.: 13/077,282

(22) Filed: Mar. 31, 2011

Related U.S. Application Data (60) Provisional application No. 61/319,761, filed on Mar. 31, 2010.

(51) Int. Cl.
*A61N 1/36021* (2006.01)
*A61H 23/02* (2006.01)

(52) U.S. Cl.
USPC .................................. 607/46; 601/46; 601/47

(58) Field of Classification Search
USPC ........................................ 607/46; 601/46, 47
See application file for complete search history.

(56) References Cited

U.S. PATENT DOCUMENTS

| | | |
|---|---|---|
| 2,821,191 A | 1/1958 | Pall |
| 3,585,991 A | 6/1971 | Balamth |
| 3,689,709 A | 9/1972 | Salmansohn et al. |
| 4,064,376 A | 12/1977 | Yamada |
| 4,779,615 A | 10/1988 | Frazier |
| 4,989,605 A | 2/1991 | Rossen |
| 5,101,810 A | 4/1992 | Skille et al. |
| 5,807,287 A | 9/1998 | Cheng |
| 5,951,500 A | 9/1999 | Cutler |
| 6,027,463 A * | 2/2000 | Moriyasu ........................ 601/46 |
| 6,104,820 A | 8/2000 | Soza |
| 6,120,468 A | 9/2000 | Tseng |
| 6,369,312 B1 | 4/2002 | Komatsu |

FOREIGN PATENT DOCUMENTS

| WO | 2007149936 A3 | 12/2007 |
|---|---|---|

* cited by examiner

*Primary Examiner* — Christopher D Koharski
*Assistant Examiner* — Michael Carey
(74) *Attorney, Agent, or Firm* — Waddey & Patterson; Gary L. Montle (57) ABSTRACT

A system for delivering dynamic electrical impulses to a recipient includes an audio input source, a user interface, and a control device. The audio input source provides an audio signal representing a pre-recorded audio composition and high-frequency audio marks mixed therewith. The device includes an audio circuit branch which receives the audio signal and provides a commensurate audio output. A cadence timing circuit also receives the audio signal, filters sequences of audio marks from the audio signal, and generates electrical impulses in accordance with the filtered signals. A pulse width adjustment circuit regulates pulse widths of the electrical impulses in response to a user-selectable input setting. An output circuit provides the pulse-width-adjusted electrical impulses across a plurality of output terminals. A plurality of electrode pads are shaped for positioning on the recipient's body and coupled to the plurality of output terminals to receive the electrical impulses.

20 Claims, 6 Drawing Sheets

MULTI-SENSORY SYSTEM AND METHOD FOR PROVIDING NEUROMUSCULAR STIMULATION

CROSS-REFERENCES TO RELATED APPLICATIONS

This application claims benefit of the following patent application(s) which is/are hereby incorporated by reference: U.S. Provisional Patent Application No. 61/319,761, filed on Mar. 31, 2010.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

BACKGROUND OF THE INVENTION

The present invention relates generally to systems and methods for providing multisensory treatment for pain reduction and relaxation therapy. More particularly, the present invention relates to a therapeutic system for delivering electrical stimulation to a user in conjunction with audio signal tempo.

Electroanalgesia is a form of pain treatment that relies on the internal or external application of electricity to a user's body. Generally stated, electroanalgesia seeks to prevent pain signals from traveling from the local point of pain origin to the brain. One form of electroanalgesia as is commonly known in the art is transcutaneous electrical nerve stimulation (TENS), the administration of which can treat various forms of pain or otherwise generate relaxing or pleasurable responses in the user in a manner often described as somewhat similar to those which are commonly attributed to acupuncture. It is generally accepted that the human body is favorably responsive to various predetermined and discrete frequencies. Devices using TENS are therefore known to achieve this end by producing pulsating transcutaneous energy to an output electrode system positioned across various portions of the user's body.

Conventional TENS applications use a high stimulation frequency (e.g., 50-150 Hz) and a low intensity current (e.g., 1-2 mA), which is the most tolerable treatment option for the broadest spectrum of users. Other applications are more analogous to acupuncture and may use a low stimulation frequency (e.g., 1-5 Hz) but a high intensity current (e.g., 15-80 mA), which works better for some users than the conventional application but is generally intolerable. An alternative TENS method applies low-intensity stimuli in high-frequency bursts. A variation of TENS methods is transcutaneous acupoint electrical stimulation (TAES), which provides stimulation by alternating high- and low-frequency electrical current in a manner known as dense-disperse.

Another modality is known as percutaneous electrical nerve stimulation (PENS) and inserts exceedingly thin probes into muscle or tissue positioned at internal dermatomal levels rather than using conventional electrodes on the exterior of the body. Such systems therefore bypass skin impedance and provide more direct electrical stimuli.

Yet another electrical stimulation modality known as interferential current therapy (IFC) sums a pair of alternating current signals having a constant intensity but a slightly different frequency to produce a current having a sinusoidal modulation in amplitude at a third (beat) frequency equal to a difference between the frequencies of the pair of signals. When the pair of frequencies are in phase with each other, the current has a relatively high amplitude with respect to conventional TENS applications and a stronger, deeper stimulation may be provided as a result.

IFC modality is an example of burst-modulated alternating current (BMAC) stimulation, as opposed to pulsed current (PC). Another example of BMAC stimulation is Russian current electrical stimulation, which conventionally applies 2.5 kHz alternating current in 50-Hz rectangular bursts of 10 ms duration and with a burst duty cycle of 50%. Recent research in the art has indicated that sensory, motor and pain thresholds may decrease to a plateau with increasing burst duration up to about 10 ms, with no further decrease. However, of burst duration plateaus were found to be different for the various thresholds, meaning that there may be optimal burst durations (e.g., 2-3 ms) where the pain/sensory threshold and pain/motor thresholds are at their maximum and which are dramatically shorter than those typically used in clinical treatment.

User comfort during treatment can vary depending on the pulse intensity and further according to the user him/herself. Intensity is a function of the pulse width and amplitude, where higher pulse intensities are generally less comfortable. In addition users have been found to independently prefer particular pulse frequencies within a given range associated with a particular application. It would be desirable to provide an electrical stimulation system which could therapeutically relax users and alleviate undesirable symptoms across an array of frequencies and below threshold pulse intensities.

Conventional systems and methods for applying electrical stimulation therapy as described herein and as generally known in the art are essentially steady and linear in nature, using a constant current stimulator to inhibit variations in impedance which may otherwise further undesirably result in increased current intensity. It would further be desirable and potentially more therapeutic to provide a delivery method originating from a more organic source such as rhythm or music and yet still inhibiting the increases in current intensity.

BRIEF SUMMARY OF THE INVENTION

A multi-sensory therapeutic delivery system and method in accordance with the present invention delivers electrical neuromuscular stimulation and treatment through the synchronization of symmetrical and periodic impulses with audio rhythm. In various aspects, the present invention may provide treatment using therapeutic systems of delivery including transcutaneous or percutaneous electroanalgesia and tactile/vibratory stimulation reaching a wide array of modalities including chiropractic, rehabilitative/pain management, and neuroscience research, as well as relaxation and sound therapies.

The frequency of delivered electrical impulse is synchronized with audio signal tempo, such that the recipient hears audio while also receiving a symmetrical and metronomic electrical impulse at a preset rate. Systems and methods in accordance with embodiments of the present invention introduce a process of encoding, within a digital audio medium, high-frequency and short-duration audio marks which are inaudible to humans and in tempo with the audio source. The system then filters these hash marks and accordingly steps electrical impulses to associated electrodes.

In an embodiment of the present invention, a device for delivering dynamic electrical impulses based on an audio input signal includes an audio input terminal coupled to receive the audio input signal from an audio input source. A first circuit branch is coupled on a first end to the audio input terminal and provides an audio output signal responsive to the audio input signal. A second circuit branch is coupled on a first end to the audio input terminal and outputs electrical impulses based on the audio signal. A cadence timing circuit filters sequences of audio marks from the audio input signal and generates electrical impulses in accordance with the filtered signals. A pulse width adjustment circuit regulates pulse widths of the electrical impulses in response to a user-defined input parameter. An output circuit provides the pulse-width-adjusted electrical impulses across a plurality of output terminals.

In another embodiment of the present invention, a system for delivering dynamic electrical impulses to a recipient includes an audio input source, a user interface, and a control device. The audio input source provides an audio signal representing a pre-recorded audio composition and high-frequency audio marks mixed therewith. The device includes an audio circuit branch which receives the audio signal and provides a commensurate audio output. A cadence timing circuit also receives the audio signal, filters sequences of audio marks from the audio signal, and generates electrical impulses in accordance with the filtered signals. A pulse width adjustment circuit regulates pulse widths of the electrical impulses in response to a user-selectable input setting. An output circuit provides the pulse-width-adjusted electrical impulses across a plurality of output terminals. A plurality of electrode pads are shaped for positioning on the recipient's body and coupled to the plurality of output terminals to receive the electrical impulses.

DETAILED DESCRIPTION OF THE INVENTION

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may.

The term "coupled" means at least either a direct electrical or mechanical connection between the connected items or an indirect connection through one or more passive or active intermediary devices. The term "circuit" means at least either a single component or a multiplicity of components, either active and/or passive, that are coupled together to provide a desired function. The term "signal" as used herein may include any meanings as may be understood by those of ordinary skill in the art, including at least one current, voltage, charge, temperature, data or a state of one or more memory locations as expressed on one or more transmission mediums.

The terms "switching element" and "switch" may be used interchangeably and may refer herein to at least: a variety of transistors as known in the art (including but not limited to FET, BJT, IGBT, JFET, etc.), a switching diode, a silicon controlled rectifier (SCR), a diode for alternating current (DIAC), a triode for alternating current (TRIAC), a mechanical single pole/double pole switch (SPDT), or electrical, solid state or reed relays.

Terms such as "providing," "processing," "supplying," "determining," "calculating" or the like may refer at least to an action of a computer system, computer program, signal processor, logic or alternative analog or digital electronic device that may be transformative of signals represented as physical quantities, whether automatically or manually initiated.

The term "controller" or "control circuit" as interchangeably used herein may refer to at least a general microprocessor, an application specific integrated circuit (ASIC), a digital signal processor (DSP), a microcontroller, a field programmable gate array, or various alternative blocks of discrete circuitry as known in the art, designed to perform functions as further defined herein.

Referring generally to FIGS. 1-6, various systems and methods may be described herein for delivering audio and electrical impulse outputs to a recipient, commensurate with a real-time audio input signal. Where the various figures may describe embodiments sharing various common elements and features with other embodiments, similar elements and features are given the same reference numerals and redundant description thereof may be omitted below.

Figure 1:
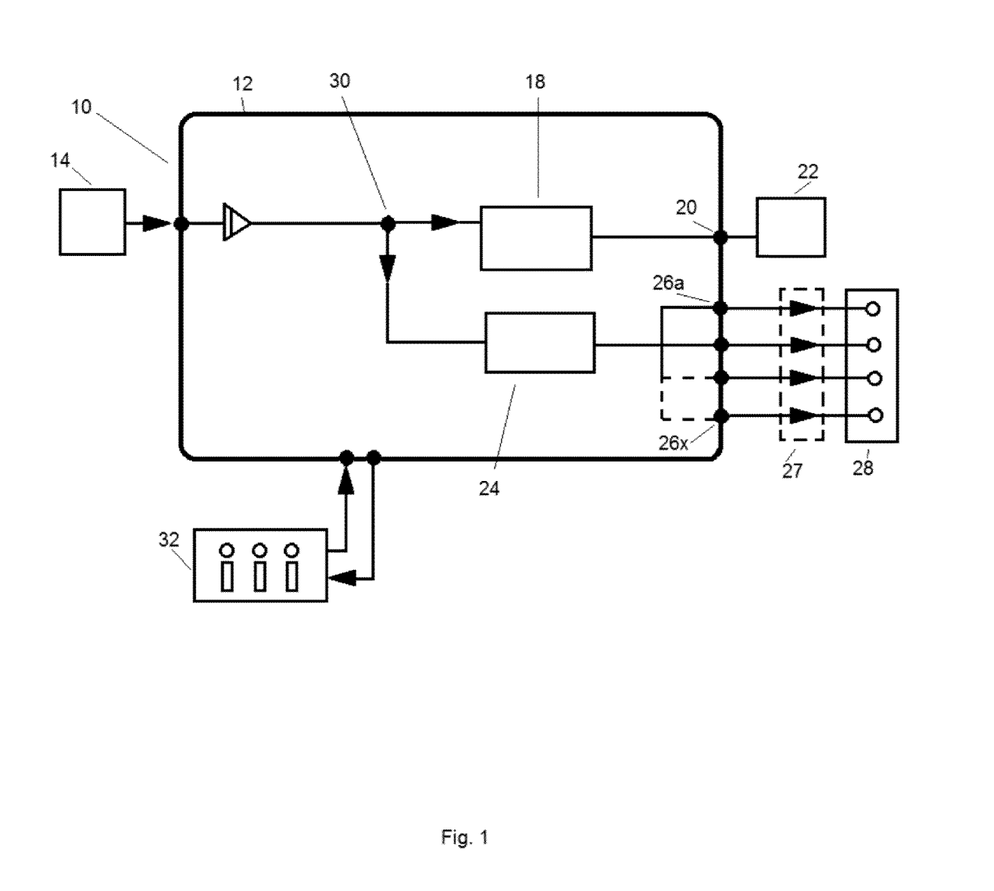
FIG. 1 is a block diagram representing an embodiment of the system of the present invention.

Referring first to FIG. 1, various embodiments of a system 10 in accordance with the present invention may include a device 12 which is configured to receive an audio input signal from an audio source 14, and to generate both audio and electrical impulse output signals based on and in accordance with the audio input. The audio output signals may be provided from an audio output terminal 20 to a conventional listening device 22 such as for example headphones. The electrical output impulses may be provided from a plurality of electrical output terminals 26a, 26b . . . 26x to a like plurality of application units 28 such as for example electrodes 28 which are shaped for positioning on the body of a recipient.

A user interface 32 may be a stand-alone unit coupled to the device 12 or alternatively may integrally reside within or in association with the device 12, such that user input settings may be provided from the user interface 32 to the device and one or more signals further provided from the device 12 to for example illuminate light-emitting diodes as indicators of device status.

Figure 2:
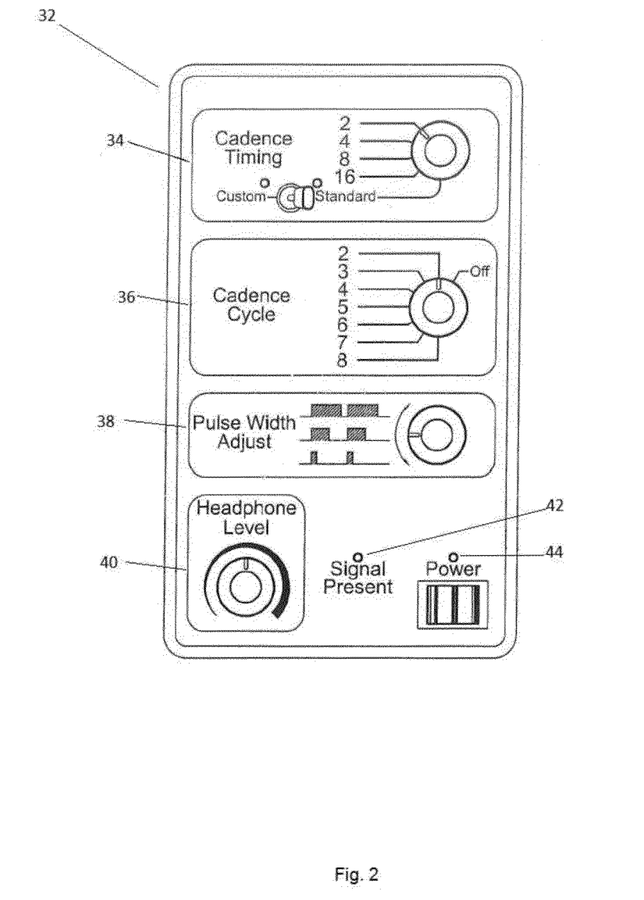
FIG. 2 is a front view representing an embodiment of a user interface from the system of FIG. 1.

Referring to FIG. 2, in an embodiment the user interface 32 may be configured with one or more of a cadence timing selection module 34 effective to provide a cadence timing user setting (for example either or a custom or standard cadence timing mode as further described below, and one of a plurality of variable cadence timing settings when in the standard mode); a cadence cycling selection module 36 effective to provide a cadence cycling user setting (for example either in an "off" mode or in an "on" mode as further described below and associated with one of a plurality of variable user settings); a pulse width adjustment selection module 38 effective to provide a pulse width adjustment user setting; and an audio volume selection module 40 effective to provide an audio volume level setting. The user interface 32 may further be configured to receive signals from the device representative of an audio signal being present in the device and of power being applied to the system, with respective indicators associated with the device signals such as for example light-emitting diodes 42, 44, respectively.

In embodiments of the device 12 of the present invention as shown in FIG. 1, an audio input signal from the audio source 14 is received at an audio input terminal 16. An audio pre-amplifier 34 may be coupled to the audio input terminal 16 on a first end and to a circuit node 30 on a second end. A first (audio) circuit branch 18 is coupled to the circuit node 30 (or otherwise stated to the audio input terminal 16) and is effective to configure the audio input signal into an audio output signal at the audio output terminal 20, the audio output signal having characteristics such as for example a desired volume as determined by an associated user input setting received from the user interface 32.

A second (electrical impulse) circuit branch 24 is also coupled to the circuit node 30 (or otherwise stated to the audio input terminal 16) and is effective to configure the audio input signal into a plurality of electrical output impulses at the output terminals 26, each of which may be associated with and provide the electrical impulses to the plurality of electrodes 28 for application to the recipient. The electrical impulses generated and provided by the second circuit branch 24 may in various embodiments have certain characteristics such as for example a pulse length as determined by an associated user input setting received from the user interface 32.

In various embodiments of the system 10, as few as a single pair of electrodes or as many as for example 128 electrodes or acupuncture interfacing clips may be provided. The device may in an embodiment have a housing which is adapted to store the electrodes or clips in a releasable and retractable manner, or may alternatively have a plurality of output terminals to which an external set of electrodes or clips may be coupled as desired.

The audio source 14 may be an external source coupled to an input terminal 16 of the device 12, the external source storing an audio composition and effective to provide an audio signal representative of the audio composition to the device 12. The audio source 14 may alternatively be a docking station residing within or in association with the device and effective to receive an external device which stores the audio composition, such that an audio input signal is provided by the audio source 14 to the remainder of the device 12 via the coupled external device. The external device storing the audio composition may take on various forms including for example a digital audio player or portable media player (e.g., MP3, iPod, etc.), but further including a memory medium such as an optical compact disc or the like, with the docking station taking on various forms to receive a desired range of such players or media.

Figure 3:
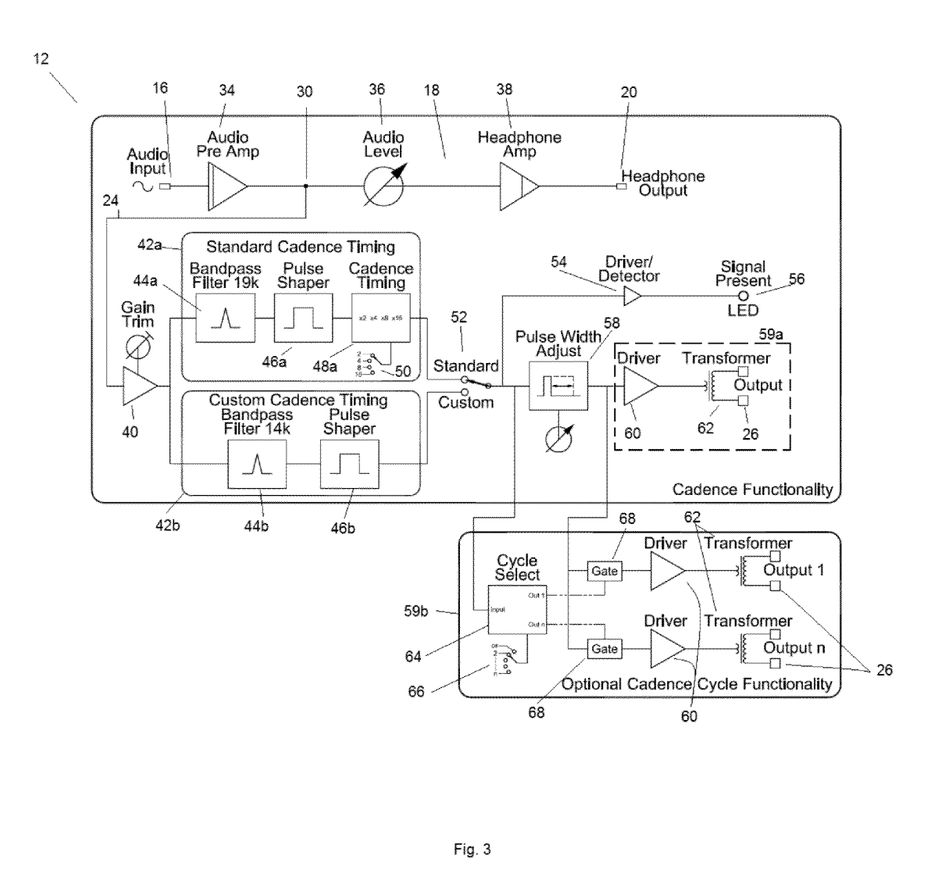
FIG. 3 is a circuit block diagram representing an embodiment of the device from the system of FIG. 1.

Referring now to FIG. 3, various embodiments of the device 12 in accordance with the present invention may be configured to deliver electrical impulses to a recipient having a cadence timing generated using either of a standard cadence timing circuit or a custom cadence timing circuit based on a cadence timing mode user input setting from the user interface as shown for example in FIG. 2, or alternatively as individually supplied with the device 12 to the exclusion of the other (such an embodiment not shown but as may be an obvious variant of the circuit in FIG. 3). In such embodiments the device 12 may be configured to substantially match the electrical impulse signature of a conventional TENS unit as closely as possible with regards to pulse widths and frequencies for the electrical impulses alongside and synchronized with the audio output. It may be anticipated that a uniform and repeatable impulse may be required for this type of Class 2 medical device, such as for example by the Food and Drug Administration. As such, various embodiments of the device 12 are configured to detect high-frequency audio hash marks (e.g., 14 kHz custom cadence and/or 19 kHz standard cadence) which have been pre-recorded and mixed into the audio composition (and accordingly into the representative audio input signal). These markings may be recorded for example in $16^{th}$ note sequences along and in tempo with the underlying audio composition.

The first circuit branch 18 in an embodiment as shown may include an audio level adjustment circuit 36 which increases or decreases characteristics of the audio input signal along the first circuit branch 18 in response to for example a variable audio volume level setting provided by the user/recipient and accordingly received from the user interface 32. The audio level adjustment circuit 36 may be embodied for example using a variable resistance coupled to a particular input terminal associated with the user interface, but those of skill in the art may comprehend various additional and alternative means for accomplishing the same function. An amplifier 38 may further be coupled between the audio level adjustment circuit 36 and the audio output terminal 20, wherein the audio output signal is provided to the listening device 22 for use by the recipient, in real-time and in accordance with the one or more user input settings.

The second circuit branch 24 in an embodiment as represented in FIG. 3 may include a gain trim circuit 40 coupled on a first end to the common circuit node 30 and effective to modify the audio input signal in accordance with predetermined gain settings. The gain trim may be adjusted for example during installation or a calibration procedure, using for example a gain potentiometer or the like that is positioned inside of a device housing and coupled to the second circuit branch 24. Alternatively, the gain trim function may be operatively linked to an external control device or even to the user interface in various embodiments (not shown).

The audio input signal then proceeds to a cadence timing circuit which may as alluded to above be either of a standard cadence timing circuit 42a or a custom cadence timing circuit 42b depending on a selected cadence timing mode. A switching element 52 may be provided in series with parallel circuit branches each containing one of the standard or custom circuits, such that the audio input signal is acted upon by one or the other depending on the switch setting as modulated in accordance with the user input. Alternatively, the device 12 may include only one of the standard or custom cadence timing circuits 42a, 42b, in which case the switch and the associated user input settings would of course be redundant. Further, additional cadence timing circuits may be made available in which case one or more switching elements may be arranged and configured to switch between the various parallel circuit branches as needed.

An exemplary standard cadence timing circuit 42a as represented in FIG. 3 may include an analog band pass filter 44a and pulse shaping circuit 46a collectively effective to pull audio marks (e.g., at a first predetermined frequency such as 19 kHz) from real-time streaming audio signals, and to step up and output the signals as electrical impulses. Various additional or alternative circuitry as is presently known in the art may be provided in accordance with the present invention for the same purpose. A frequency divider circuit 48 may be coupled in series with the pulse shaping circuit 46a to adjust the output frequency of the electrical impulses from $16^{th}$ to whole note arrays based on for example the cadence timing user input setting received from the user interface 32.

An exemplary custom cadence timing circuit 42b as represented in FIG. 3 may include an analog band pass filter 44b and pulse shaping circuit 46b collectively effective to pull audio marks (e.g., at a second predetermined frequency such as 14 kHz) from real-time streaming audio signals, and to step up and output the signals as electrical impulses. The first and second predetermined frequencies as previously described are not expressly limited to any particular frequencies or range of frequencies, but generally will at least be sufficiently distinct from each other that a person of skill in the art may provide band pass filters for a standard cadence timing circuit 42a and for a custom cadence timing circuit 42b capable of distinguishing between audio marks intended for either configuration without requiring overly complex circuitry. The audio marks may in such embodiments generally have been previously mixed into the composition commensurate with audio dynamics and nuance, such that for example a composition of the Barber of Seville Overture so adapted may include audio hash marking at eighth-note sequences matching strings in melody followed by quarter-note spaced markings. The hash marks in the modified composition may desirably of course be inaudible to the human ear such that the audio output signals generated from the composition may be substantially indistinguishable by the recipient from an original or unmodified composition.

The custom cadence timing circuitry is further effective thereby to generate electrical impulses at the frequencies associated with the audio marks rather than at a consistent predetermined or otherwise user-selectable frequency. Various additional or alternative circuitry as is presently known in the art may be provided in accordance with the present invention for the same purpose.

A signal detection circuit 54 may in various embodiments as shown be coupled to the second circuit branch 24 and effective for example to generate a first or second signal status state at a status output terminal 56. When the signal is detected thereby, an LED indicator or the equivalent on the user interface which is coupled to the status output terminal 56 may be configured to light up or otherwise indicate the presence of the electrical impulse signals on the second circuit branch 24.

A pulse width adjustment circuit 58 may further be coupled to the cadence timing circuit(s) 42 and effective to adjust the lengths of the electrical impulses in accordance with the pulse width adjustment user setting from the user interface 32 (where applicable). Alternatively, or perhaps in addition to the user setting feature in a switchable setting, the pulse width setting may be adjusted using a trim potentiometer or the equivalent residing within or in association with the device housing such that is set during installation or subsequent calibration and maintained accordingly. The pulse width adjustment circuit 58 may take on various forms as are presently known in the art and standard in many conventional TENS applications to set the lengths of the electrical impulses for example within a range of about 30 micro-seconds to 3 milli-seconds.

An output circuit 59a may be coupled to the pulse width adjustment circuit 58 and effective to provide the final electrical impulses to a plurality of output terminals 26, to which the application tools 28 such as electrodes 28 may be coupled for the purpose of applying the electrical impulses to a recipient. The output circuit 59a in an embodiment as represented includes a signal driver 60 coupled to a primary winding for a transformer 62, the secondary winding of which is coupled on either end to first and second output terminals 26a, 26b, respectively, so as to generate an output electrical impulse across the output terminals 26a, 26b. While only a single driver 60 and transformer 62 are illustrated in association with the output circuit 59a, it is anticipated that a plurality of output circuit branches may be provided in parallel with each other and coupled in series with the pulse width adjustment circuit, such that a common electrical impulse is generated across each of a plurality of output terminal pairs.

In another embodiment of the output circuit 59b (also represented on FIG. 3), a cadence cycling control circuit 64 may be coupled on a first end to the second circuit branch 24 between the cadence timing circuit 42 and a first end of the pulse width adjustment circuit 58, and cycle the electrical impulses through an array of output circuit branches in accordance with a cadence cycling user setting 66 (for example either in an "off" mode or in an "on" mode and associated with one of a plurality of variable user settings). The cycling control circuit 64 may be formed of a ring counter integrated circuit effective to output and cycle through multiple output circuit branches (and associated electrode pairs) at a frequency set by the standard cadence timing user setting, or alternatively as determined by the custom cadence timing circuit based on the filtered audio marks. Each output circuit branch in the cadence cycling embodiment as represented in FIG. 3 further may include a gate 68 arranged to receive an associated output from the control circuit 64 and further coupled to the second circuit branch 24 on a second end of the pulse width adjustment circuit 58. An output from the gate 68 is provided to a driver circuit 60 and subsequently to a primary winding of a transformer 60 in substantially equivalent manner to that described above with respect to output circuit 59a, with the exception being the cycling of the output signals across the output circuit branches rather than the consistent application to each branch.

In alternative embodiments the output signals may be arranged to cycle sequentially along each output circuit branch or randomly, pseudo-randomly, or in a predetermined sequence or combination that is selected or programmed to correspond with an expected position on the body of the recipient for electrodes associated with the respective output branches. Where for example it has been determined that particular portions of a composition will provide greater or lesser electrical impulse intensity levels, it may be desirable to program the cycling feature such that particular areas of the body are stimulated in accordance with the greater or lesser intensity to maximize the intended effects.

Figure 4:
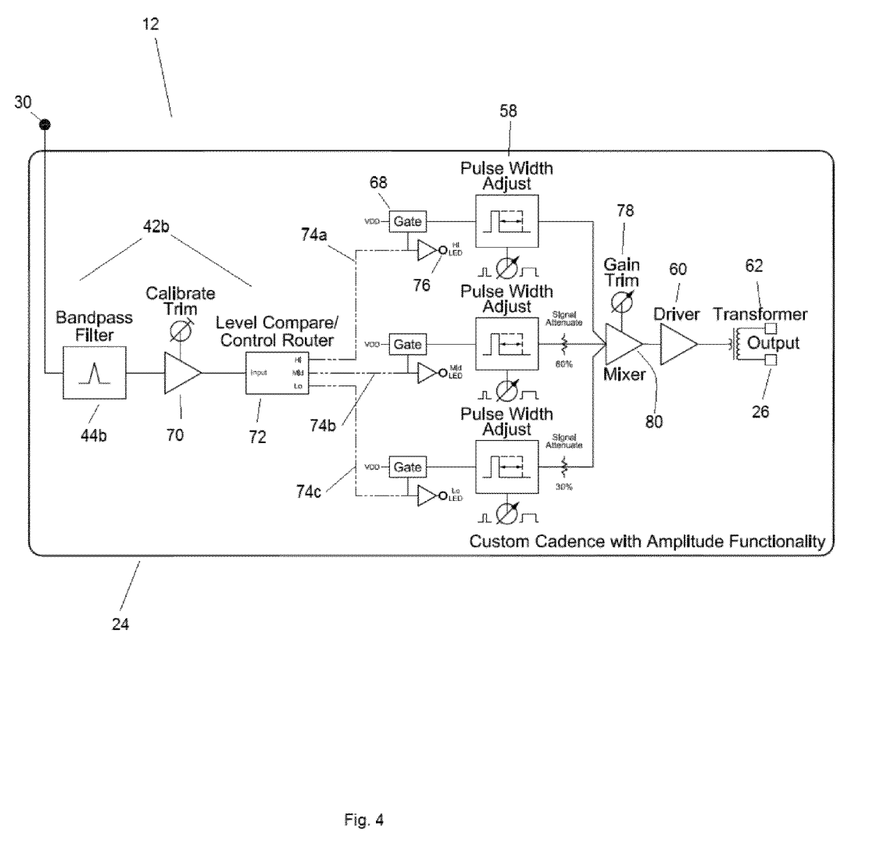
FIG. 4 is a circuit block diagram representing an embodiment of the device from the system of FIG. 1 including a custom cadence timing circuit having amplitude mode functionality.

Referring now to FIG. 4, in an embodiment the second circuit branch 24 may include a custom cadence timing circuit 42b having an amplitude modulation feature wherein the generated electrical impulses are modulated based on the filtered audio marks to reflect the amplitude dynamic of the original audio signal. The amplitude of the electrical impulses may be modulated among various amplitude modes as determined from the audio hash marks, which in an embodiment as shown include high (Hi), normal (Mid) and low (Lo). A band pass filter 44b as previously described is provided to filter the audio marks (e.g., having a frequency of 14 kHz) from the audio signal. A calibrate trim circuit 70 is coupled to the filter 44b and effective to modify the filtered signal in accordance with predetermined trim settings. The calibration may be adjusted for example during installation or a subsequent calibration procedure, using for example a trim potentiometer or the like that is positioned inside of the device housing and coupled to the second circuit branch 24. Alternatively, the calibration trim function may be operatively linked to an external control device or even to the user interface 32 in various embodiments (not shown).

An amplitude level control circuit 72 may be coupled to receive an output from the calibrate trim circuit 70 and effective to route the electrical impulse in accordance with the determined amplitude mode to an associated amplitude control branch 74a, 74b, 74c, respectively. Each branch 74a, 74b, 74c as shown includes a gate circuit 68 and pulse width adjustment circuit 58 having functionality substantially as described with respect to previous embodiments above, such that resulting electrical impulses generated at a signal mixing circuit 80 have an amplitude commensurate with the hash marks filtered from the underlying audio signal. An indicator 76 such as for example an LED may be coupled to each of the amplitude control branches 74a, 74b, 74c to provide an external indication either for example on the user interface, an external indicator on the housing of the device or any alternative and equivalent location. The signal mixing circuit 80 generates an output electrical impulse to a driver circuit 60 based on the received signals from the amplitude control branches 74a, 74b, 74c and further on a gain trim setting from a gain trim circuit 78, which may for example be formed of a potentiometer or the equivalent which is user-adjustable and residing within or in association with the device housing.

Embodiments of the present invention as represented in FIGS. 3-4 may generally relate to a device 12 for use in for example consumer applications of the electroanalgesic market which includes the conventionally known and aforementioned TENS units. Alternative embodiments as described below with respect to FIGS. 5-6 may relate to a device 12 for use in clinical applications that takes its cues from a "live performance" by a practitioner. The impulse delivery sequence is thereby created and controlled by the practitioner or an equivalent user in such embodiments, rather than from determined from a pre-recorded audio composition having audio hash marks mixed therewith.

Figure 5:
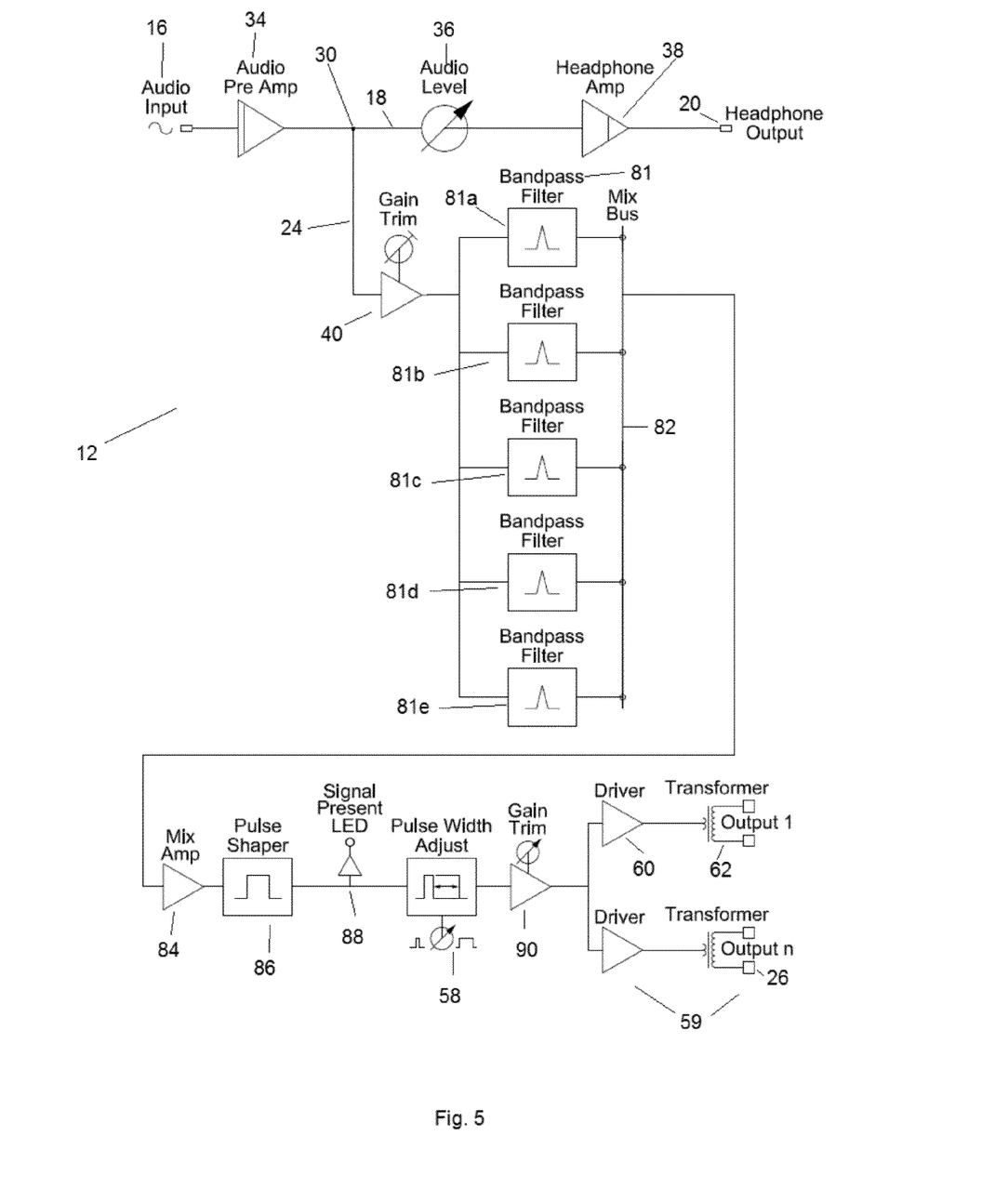
FIG. 5 is a circuit block diagram representing another embodiment of the second circuit branch of the system of FIG. 1 including a frequency cycling functionality.

Referring first to FIG. 5, a device 12 may be provided to receive a "live" audio input signal at an audio input terminal 16 from an audio source 14 which may include for example percussion, wind, vocal and even biometric frequencies, such as heartbeat or electroencephalographic frequencies. In similar fashion to various embodiments of a device 12 as previously described with respect to consumer applications, a first circuit branch 18 is coupled to the common node 30 and effective to provide an audio output signal at the audio output terminal 20. The second circuit branch 24 in a "clinical" embodiment as represented in FIG. 5 includes a gain trim circuit 40 coupled to the common node 30 but otherwise differs substantially from that of the "consumer" embodiments described above.

A plurality of band pass filters 81 are coupled in parallel between the gain trim circuit 40 and a common signal mixing bus 82 to allow the "live" audio signal to be filtered, stepped up and output as an electrical impulse. The practitioner or equivalent user may set the band pass filters 81 using a variable frequency input setting (not shown) to generate electrical impulses in accordance with for example an intended instrument/modality frequency range. As one example, if the recipient intends to listen to a music composition with a heavy kick drum, the frequency filters may be set to a low setting to allow for maximum rhythmic output to the electrodes. To take another example, however, if Flight of the Bumble Bee (chosen here for its relatively frenetic pacing) is to be played the user may set the frequency filters to a lower middle setting. An exemplary range for frequency settings may be from 20 Hz to 10 kHz.

A mixing amplifier 84 is coupled on a first end to receive the signals from the mixing bus 82, and on a second end to a pulse shaping circuit 86. A pulse width adjustment circuit 58 may be coupled to the pulse shaping circuit 86 and effective to adjust the lengths of the electrical impulses based on a pulse width setting from for example the user interface. A signal detector 88 may be coupled to the second circuit branch 24 and effective to provide a signal status to an indicator located on the user interface, device housing or otherwise externally located but functionally linked to the detector 88. A second gain trim circuit 90 may be coupled on a first end to receive the pulse width adjusted electrical impulses and on a second end to an output circuit 59 having one or more output circuit branches. Each output circuit branch includes a driver circuit 60 coupled to the primary winding of a transformer 62, with the secondary winding of the transformer 62 being coupled on either end to first and second output terminals 26, the output circuit branches thereby collectively defining a like plurality of output terminal pairs and associated electrical impulse outputs.

Figure 6:
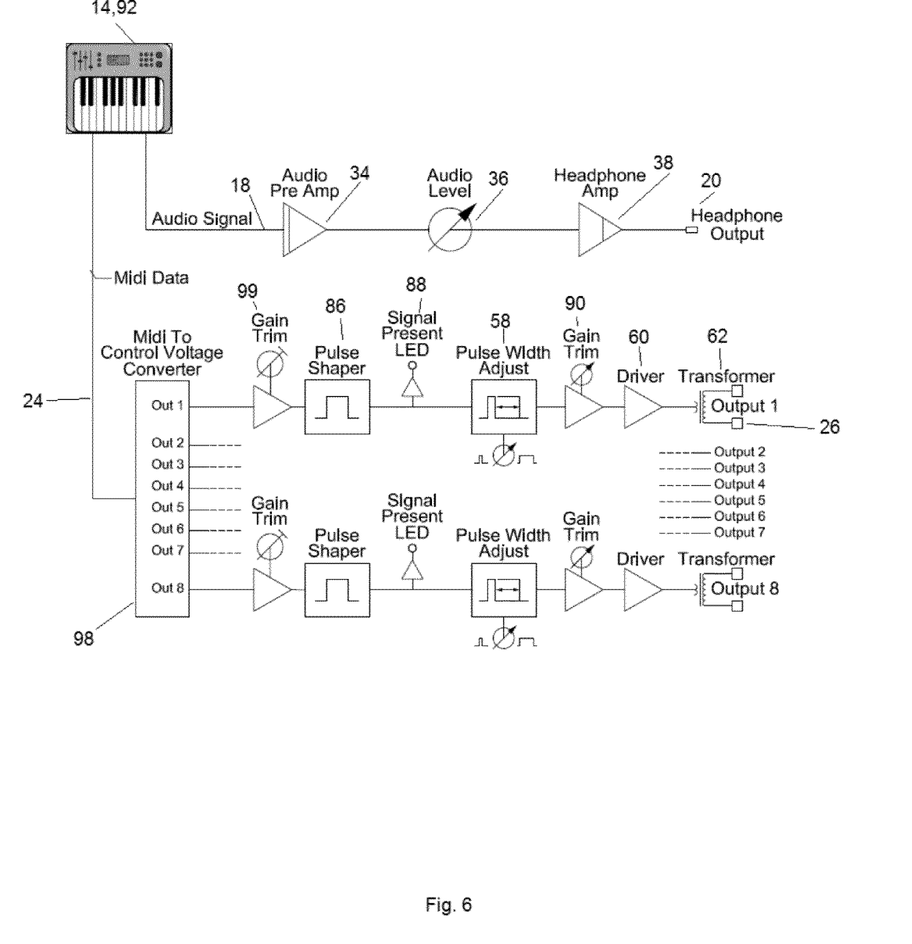
FIG. 6 is a circuit block diagram representing another embodiment of the second circuit branch of the system of FIG. 1 including a frequency filtering functionality.

Referring now to FIG. 6, a device 12 may be provided to receive an audio input signal at an audio pre-amplifier 34 on a first (audio) circuit branch 18 from an audio source 14 such as a Musical Instrument Digital Interface (MIDI) controller 92 as is known in the art. Specific ranges on the MIDI controller 92 (e.g., a keyboard or any equivalent MIDI trigger such as a drum system) can be programmed to generate and send MIDI data signals to the second circuit branch 24 which are then stepped up and output as electrical impulses to distinct regions of output terminals in various arrays. In embodiments as shown, the MIDI controller audio output signal and MIDI data output signal to the second circuit branch are provided separately rather than to a common node in the device as described with respect to previous embodiments, but may still generally result in a commensurate audio output signal with respect to the output electrical impulses.

The second circuit branch 24 includes a MIDI converter control circuit 98 which is coupled to receive the MIDI data signal on a first end and converts the MIDI data signal into a plurality of output signals provided to a like plurality of output branches coupled to the control circuit 98. In an embodiment, one of three amplitude settings—low, medium or high—can be set and modulated via the MIDI controls.

Each output branch in an embodiment as represented in FIG. 6 includes a first gain trim circuit 99, a pulse shaping circuit 86, a signal detector 88, a pulse width adjustment circuit 58, a second gain trim circuit 90, a driver 60, a transformer 62 and first and second output terminals 26, each component of which has substantially the same general function as described with respect to previous embodiments.

The previous detailed description has been provided for the purposes of illustration and description. Thus, although there have been described particular embodiments of the present invention of a new and useful "Electro-Audio Neuromuscular Stimulator," it is not intended that such references be construed as limitations upon the scope of this invention except as set forth in the following claims.

What is claimed is:

1. A device for delivering dynamic electrical impulses based on a pre-recorded audio input signal, the device comprising:
   an audio input terminal coupled to receive the audio input signal from an audio input source;
   a first circuit branch coupled on a first end to the audio input terminal and effective to provide an audio output signal responsive to the audio input signal;
   a second circuit branch coupled on a first end to the audio input terminal and further comprising
      a cadence timing circuit effective to filter sequences of audio marks from the audio input signal, said audio marks having been mixed into the audio input signal and comprising a frequency substantially above that of the audio input signal, and generate electrical impulses in accordance with the filtered signals, a pulse width adjustment circuit effective to regulate pulse widths of the electrical impulses in response to a user-defined input parameter, and an output circuit effective to provide the pulse-width-adjusted electrical impulses across a plurality of output terminals.

2. The device of claim 1, the output circuit comprising a plurality of output circuit branches each comprising one or more output terminal pairs of said plurality of output terminals; and a cadence cycling control circuit effective to cycle electrical impulses across one or more of the plurality of output circuit branches in accordance with each sequence of audio marks.

3. The device of claim 2, the cadence timing circuit further effective to define a normal, low or high amplitude mode based on an amplitude range specified in each filtered sequence of audio marks in the audio input signal, and to generate electrical impulses in accordance with the defined amplitude mode.

4. The device of claim 3, the user-defined input parameter to which the pulse width adjustment circuit is responsive further comprising a first user-defined input parameter, the cadence timing circuit further comprising a custom cadence timing circuit operable in response to a first mode of a second user-defined input parameter, the second circuit branch further comprising a standard cadence timing circuit operable in response to a second mode of the second user-defined input parameter, the standard cadence timing circuit effective to filter sequences of audio marks from the audio input signal at a frequency defined by the second user-defined input parameter, and to generate electrical impulses in accordance with the filtered signals.

5. The device of claim 4, the standard cadence timing circuit further comprising a frequency divider chip responsive to an input signal corresponding to the user-defined input parameter.

6. The device of claim 5, the standard cadence timing circuit further comprising a band pass filter effective to pull audio marks having a first predetermined frequency from the audio input signal, and the custom cadence timing circuit further comprising a band pass filter effective to pull audio marks having a second predetermined frequency from the audio input signal.

7. The device of claim 5, the cadence cycling control circuit effective to cycle electrical impulses across one or more of the plurality of output circuit branches in accordance with each sequence of audio marks, and at a frequency set by the second user-defined input parameter in the standard cadence timing mode or at a frequency defined by the filtered audio marks in the custom cadence timing mode.

8. A system for delivering dynamic electrical impulses to a recipient, the system comprising:

an audio input source effective to provide an audio signal representing a pre-recorded audio composition and comprising a plurality of high-frequency audio marks mixed into the composition, said audio marks comprising a frequency substantially above that of the underlying audio composition;

a user interface having a user-selectable input setting associated with a desired electrical impulse length;

a device comprising an audio circuit branch coupled on a first end to receive the audio signal from the audio input source and effective to provide an audio output signal responsive to the received audio signal, a cadence timing circuit coupled to receive the audio signal from the audio input source and effective to filter sequences of audio marks from the audio input signal and generate electrical impulses in accordance with the filtered signals, a pulse width adjustment circuit effective to regulate pulse widths of the electrical impulses in response to the user-selectable input setting, and an output circuit effective to provide the pulse-width-adjusted electrical impulses across a plurality of output terminals; and a plurality of electrode pads shaped for positioning on the body of a recipient and coupled to the plurality of output terminals of the device to receive the electrical impulses.

9. The system of claim 8, the audio source comprising a docking station integrated into the device and effective to physically receive an external audio source storing the audio composition.

10. The system of claim 8, the audio source comprising a audio input interface effective to functionally link to an external audio source storing the audio composition.

11. The system of claim 8, the audio source comprising a memory medium integrated into the device and effective to receive and store the audio composition.

12. The system of claim 8, the output circuit comprising a plurality of output circuit branches each comprising one or more output terminal pairs of said plurality of output terminals; and a cadence cycling control circuit effective to cycle electrical impulses across one or more of the plurality of output circuit branches in accordance with each sequence of audio marks.

13. The system of claim 12, the cadence cycling control circuit further effective to cycle electrical impulses across one or more of the plurality of output circuit branches in accordance with a predetermined sequence defined at least in part by a part of the body of the recipient to which electrode pads associated with the output circuit branches are expected to be positioned.

14. The system of claim 12, the cadence timing circuit further effective to define a normal, low or high amplitude mode based on an amplitude range specified in each filtered sequence of audio marks in the audio input signal, and to generate electrical impulses in accordance with the defined amplitude mode.

15. The system of claim 14, the user-selectable input setting associated with a desired electrical impulse length further comprising a first user-selectable input setting, the user interface further comprising a second user-selectable input setting having a first mode and a second mode, the cadence timing circuit further comprising a custom cadence timing circuit operable in response to the first mode of the second user-selectable input setting, the second circuit branch further comprising a standard cadence timing circuit operable in response to the second mode of the second user-defined input parameter, the standard cadence timing circuit effective to filter sequences of audio marks from the audio input signal at a frequency defined by the second user-defined input parameter, and to generate electrical impulses in accordance with the filtered signals.

16. The system of claim 15, the standard cadence timing circuit further comprising a frequency divider chip responsive to an input signal corresponding to the user-defined input parameter and a band pass filter effective to pull audio marks having a first predetermined frequency from the audio input signal, the custom cadence timing circuit further comprising a band pass filter effective to pull audio marks having a second predetermined frequency from the audio input signal.

17. The system of claim 16, the cadence cycling control circuit effective to cycle electrical impulses across one or more of the plurality of output circuit branches in accordance with each sequence of audio marks, and at a frequency set by the second user-defined input parameter in the standard cadence timing mode or at a frequency defined by the filtered audio marks in the custom cadence timing mode.

18. A method of delivering dynamic electrical impulses to a recipient, the method comprising:

providing an audio signal representing a pre-recorded composition and comprising a plurality of pre-recorded high-frequency audio marks mixed therewith, said audio marks comprising a frequency substantially above that of the underlying pre-recorded composition;

receiving an input setting from a user interface;

providing an audio output signal to a listening device commensurate with the received audio signal;

filtering sequences of audio marks from the audio input signal;

generating electrical impulses in accordance with the filtered signals;

adjusting a length of the electrical impulses in response to the input setting received from the user interface; and providing the pulse-width-adjusted electrical impulses across a plurality of output terminals.

19. The method of claim 18, the step of providing the pulse-width-adjusted electrical impulses across a plurality of output terminals comprising cycling the pulse-width-adjusted electrical impulses across one or more of a plurality of output circuit branches collectively defining a plurality of output terminals in accordance with each sequence of audio marks.

20. The method of claim 19, the step of receiving an input setting from a user interface comprising receiving first and second user settings from a user interface, the step of filtering sequences of audio marks from the audio input signal comprising filtering audio marks having a first predetermined frequency from the audio input signal in a first cadence timing mode and filtering audio marks having a second predetermined frequency from the audio input signal in a second cadence timing mode, the cadence timing modes determined in accordance with the first user setting, the step of adjusting a length of the electrical impulses in response to the input setting received from the user interface comprising adjusting a length of the electrical impulses in response to the second user setting.

* * * * *